United States Patent [19]

Treuner et al.

[11] 4,168,266
[45] Sep. 18, 1979

[54] 6-[[[(2-CYANOMETHYL)AMINO]-1,2-DIOXO-ETHYL]-AMINO]ACYL PENICILLINS

[75] Inventors: Uwe D. Treuner; Hermann Breuer, both of Regensburg, Fed. Rep. of Germany

[73] Assignee: E. R. Squibb & Sons, Inc., Princeton, N.J.

[21] Appl. No.: 910,546

[22] Filed: May 30, 1978

[51] Int. Cl.$^2$ .............. C07D 499/64; C07D 499/66; C07D 499/68; C07D 499/70
[52] U.S. Cl. .............................. 260/239.1; 424/271
[58] Field of Search .................................. 260/239.1

[56] References Cited

U.S. PATENT DOCUMENTS

| | | | |
|---|---|---|---|
| 3,573,294 | 3/1971 | Long et al. | 260/243 |
| 3,997,533 | 12/1976 | Kabbe | 260/239.1 |
| 4,009,272 | 2/1977 | König et al. | 260/239.1 |
| 4,028,354 | 6/1977 | Breuer et al. | 424/246 |
| 4,073,783 | 2/1978 | Hamanaka et al. | 260/239.1 |

Primary Examiner—Gerald A. Schwartz
Attorney, Agent, or Firm—Lawrence S. Levinson; Merle J. Smith

[57] ABSTRACT

6-[[[(2-Cyanomethyl)amino]-1,2-dioxoethyl]amino]acyl pencillins which have the formula

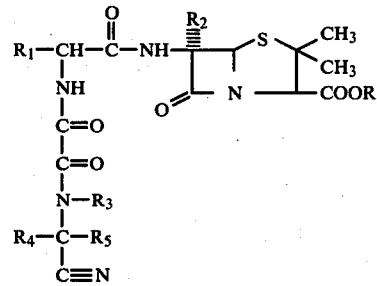

wherein R is hydrogen, lower alkyl, tri(lower alkyl)silyl, tri(lower alkyl)stannyl, trihaloethyl or a salt forming ion; $R_1$ is hydrogen, lower alkyl, saturated or unsaturated cycloalkyl, phenyl, phenyl-lower alkyl, substituted phenyl or certain heterocyclic groups; $R_2$ is hydrogen or methoxy; $R_3$ is hydrogen, lower alkyl, phenyl-lower alkyl or cycloalkyl; and $R_4$ and $R_5$ each is hydrogen or lower alkyl, are useful as antibacterial agents.

12 Claims, No Drawings

6-[[[(2-CYANOMETHYL)AMINO]-1,2-DIOXOETHYL]-AMINO]ACYL PENICILLINS

SUMMARY OF THE INVENTION

Cephalosporins and penicillins having various acyl side chains are typified, for example, in U.S. Pat. Nos. 3,573,294, 3,997,533, 4,028,354, 4,073,783 and 4,009,272. 7β-[[[(2-Cyanomethyl)amino]-1,2-dioxoethyl]amino]acyl cephalosporins are described in our copending application Ser. No. 789,467 filed Apr. 21, 1977, now U.S. Pat. No. 4,096,330, issued June 20, 1978.

This invention relates to new 6-[[[(2-cyanomethyl)amino]-1,2-dioxoethyl]amino]acyl penicillin derivatives which have the formula

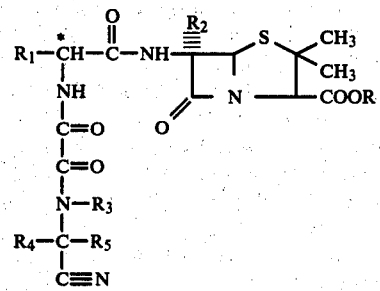

which are distinguishable from such prior art known compounds.

R represents hydrogen, lower alkyl, tri(lower alkyl)-silyl, tri(lower alkyl)stannyl, trihaloethyl or a salt forming ion.

$R_1$ represents hydrogen, lower alkyl, saturated or unsaturated cycloalkyl, phenyl, phenyl-lower alkyl, substituted phenyl or certain heterocyclic groups.

$R_2$ represents hydrogen or methoxy. The $R_2$ substituent is in the α-configuration as indicated by the broken lines.

$R_3$ represents hydrogen, lower alkyl, phenyl-lower alkyl or cycloalkyl.

$R_4$ and $R_5$ each represents hydrogen or lower alkyl.

The asterisk indicates an asymmetric carbon atom.

DETAILED DESCRIPTION OF THE INVENTION

The various groups represented by the symbols have the meanings defined below and these definitions are retained throughout this specification.

The lower alkyl groups referred to throughout this specification include straight or branched chain hydrocarbon groups containing 1 to 7 carbon atoms, preferably 1 to 4 carbons, and especially 1 or 2 carbons. Examples of the type of groups contemplated are methyl, ethyl, propyl, isopropyl, butyl, t-butyl, etc. The phenyl-lower alkyl groups include such lower alkyl groups attached to a phenyl ring, preferably benzyl and phenethyl.

The saturated and unsaturated cycloalkyl groups are the alicyclic groups having up to 7 carbons and up to 2 double bonds in the ring, i.e., the cycloalkyl groups cyclopropyl, cyclobutyl, cyclopentyl, cyclohexyl and cycloheptyl, the cycloalkenyl groups having up to 7 carbons with one double bond, cyclobutenyl, cyclopentenyl, cyclohexenyl and cycloheptenyl and the cycloalkadienyl groups having up to 7 carbons with two double bonds located at various positions such as 1,4-cyclohexadienyl which is a preferred group.

The substituted phenyl groups include one or two substituents selected from halogen (preferably chlorine or bromine), lower alkyl (preferably having 1 to 4 carbons, especially methyl or ethyl), lower alkoxy (preferably having 1 to 4 carbons especially methoxy or ethoxy), and hydroxy, e.g., 2-, 3-, or 4-chlorophenyl, 2-, 3-, or 4-bromophenyl, 2-, 3-, or 4-hydroxyphenyl, 3,5-dichlorophenyl, 2-, 3-, or 4-methylphenyl, 2-, 3- or 4-ethoxyphenyl, etc.

The salt forming ions represented by R are metal ions, e.g., aluminum, alkali metal ions such as sodium or potassium, alkaline earth metal ions such as calcium or magnesium, or an amine salt ion, of which a number are known for this purpose, for example, phenyl-lower alkylamines such as dibenzylamine, N,N-dibenzylethylenediamine, lower alkylamines such as methylamine, triethylamine, and N-lower alkylpiperidines such as N-ethylpiperidine. Sodium and potassium are the preferred salt forming ions.

The halogens are the four common halogens, of which chlorine and bromine are preferred. In the case of the trihaloethyl group represented by R, 2,2,2-trichloroethyl is preferred.

Trimethylsilyl is the preferred tri(lower alkyl)-silyl group.

The heterocyclic groups represented by $R_1$ are thienyl, furyl or pyridyl, i.e., 2-thienyl (which is especially preferred), 3-thienyl, 2-furyl, 3-furyl, 2-pyridyl, 3-pyridyl or 4-pyridyl.

The products of this invention can be produced by acylating a 6-aminopenicillanic acid derivative having the formula

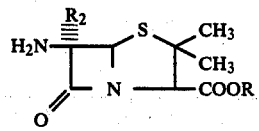

with an acid having the formula

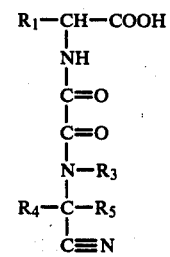

or an activated deivative like the acid halide, activated ester like the nitrophenyl ester or dinitrophenyl ester, or mixed anhydride, and/or in the presence of a coupling agent like dicyclohexylcarbodiimide.

According to an alternate method, a compound having the formula

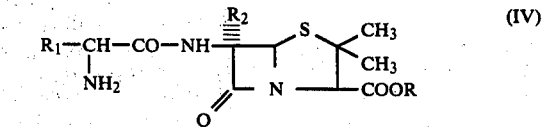

is dissolved or suspended in an organic solvent as dimethylaniline, acetonitrile, methylene chloride, chloroform, dimethylacetamide, dimethylformamide, tetrahydrofuran, dioxane, benzene or the like, and converted to an ester, for example forming the trimethylsilyl ester by reaction with bis(trimethylsilyl)-acetamide. The product is then made to react with a compound having the formula

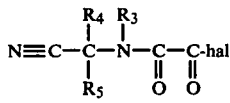
(V)

wherein hal represents a halogen, preferably chlorine, in an organic solvent like those mentioned above at a reduced temperature, e.g., about 0°C.

A modification of the foregoing involves displacing the halogen in the compound of formula V with an activating group Y, e.g., by reaction with the compound Y—OH, wherein Y is

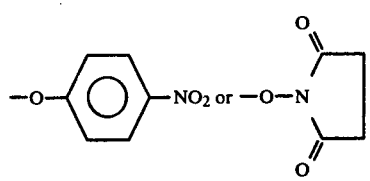

in the presence of a base and then reacting this activated ester derivative with the compound of formula IV in the presence of a base like triethylamine.

The starting material of formula III is produced from an α-amino acid ester having the formula

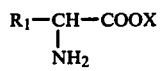
(VIII)

wherein $R_1$ has the same meaning as defined above and X is a readily removable group, e.g., diphenylmethyl, nitrophenyl, dinitrophenyl, t-butyl, trimethylsilyl or the like, which is made to react with an oxalyl halide like oxalyl chloride to form an intermediate having the formula

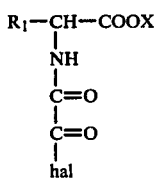
(IX)

wherein hal represents halogen, preferably chlorine, in a solvent like dioxane. This intermediate is then made to react with a compound having the formula

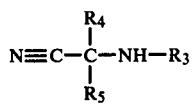
(X)

e.g., in an organic solvent like those mentioned above in the presence of an organic base like dimethylaniline at a reduced temperature, e.g., about -20° C., and treatment of this intermediate with an acid, e.g., trifluoroacetic acid and anisole, yields the free acid of formula III. By reacting the compound of formula X with an oxalyl halide like oxalyl chloride in a solvent like dioxane at an elevated temperature e.g., about 60 to 70° C., a compound of formula V is obtained.

Alternatively, the starting material of formula III can be produced from the starting material of formula VIII by reacting the latter with a compound having the formula

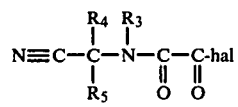
(V)

The carboxylate salts of the compound of formula I are formed by reacting the carboxyl group of the 6-aminopenicillanic acid moiety, i.e., R is hydrogen, with any of the salt forming ions described above.

It will be appreciated that the compounds of formula I are optically active due to the presence of the asymmetric carbon atom indicated by the asterisk. By selection of the appropriate starting material it is possible to obtain the compounds of formula I as a mixture of optically active isomers or isolated as a single isomer. The various isomers as well as their mixtures are within the scope of the invention.

Preferred compounds of this invention are the acids and alkali metal salts of formula I (i.e., R is hydrogen, sodium or potassium) wherein $R_1$ is cyclohexadienyl, phenyl or heterocyclic selected from 2-thienyl, 3-thienyl, 2-furyl, 3-furyl, 2-pyridyl, 3-pyridyl and 4-pyridyl; $R_2$ is hydrogen or methoxy especially hydrogen; and $R_3$, $R_4$ and $R_5$ each is hydrogen or lower alkyl, especially hydrogen, and especially the D-isomers thereof.

The most preferred final compounds are the acids and alkali metal salts of formula I wherein $R_1$ is 2-thienyl or phenyl, most especially 2-thienyl; and $R_2$, $R_3$, $R_4$ and $R_5$ each is hydrogen.

The acid compounds of formula I have a broad spectrum of antibacterial activity against both gram positive and gram negative organisms such as *Staphylococcus aureus, Streptococcus faecalis, Pseudomonas aeruginosa, Proteus rettgeri, Proteus morganii, Escherichia coli, Klebsiella pneumoniae, Serratia marcescens*, etc. They may be used as antibacterial agents to combat infections due to organisms such as those named above, and in general may be utilized in a manner similar to ampicillin and other semi-synthetic penicillins. For example, a compound of formula I or a physiologically acceptable salt thereof may be used in various animal species in an amount of about 1 to 100 mg/kg., daily, orally or parenterally, in single of two to four divided doses to treat infections of bacterial origin, e.g., 10.0 mg/kg in mice.

About 50 to 600 mg. of an acid compound of formula I or a physiologically acceptable salt thereof can be incorporated in an oral dosage form such as tablet, capsule or elixir or in an injectable form in a sterile aqueous vehicle prepared according to conventional pharmaceutical practice.

Illustrative process details are provided in the examples which are models by which additional members of the class can be prepared. Additional process details on the production of certain intermediates can also be found in our copending application identified above. All temperatures are in degrees Celsius.

EXAMPLE 1

[(Cyanomethyl)amino]oxoacetyl chloride 20 mM of cyanomethylamine hydrochloride and 25 mM of oxalyl chloride in 100 mM of absolute dioxane are heated at 60–70° while passing through a stream of nitrogen. After one hour a clear solution results and there is no evidence of hydrogen chloride in the nitrogen stream. The solvent is evaporated under vacuum and the residual, light brown oil is taken up in methylene chloride, filtered over charcoal and stored at −30° until it is to be used.

EXAMPLE 2

D-α-[[[(Cyanomethyl)amino]oxoacetyl]amino]-2-thiopheneacetic acid, diphenylmethyl ester 10 mM of 2-D-thienylglycine, diphenylmethyl ester are dissolved in 20 ml. of methylene chloride, 10 mM of dimethylaniline are added and half the product of Example 1 is added dropwise with stirring at −20°. After thirty minutes, the reaction solution is washed first with 50 ml. of 1 N hydrochloric acid and then with 50 ml. of water. After drying over sodium sulfate, it is concentrated by evaporation. A viscous yellow mass is obtained which solidifies upon treatment with ether. This is crystallized from a little ethanol to obtain D-α-[[[(cyanomethyl)amino]oxoacetyl]amino]-2-thiopheneacetic acid, diphenylmethyl ester in the form of white crystals, yield 63%, m.p. 160–161°.

EXAMPLE 3

D-α-[[[(Cyanomethyl)amino]oxoacetyl]amino]-2-thiopheneacetic acid

By treating the diphenylmethyl ester obtained in Example 2 with trifluoroacetic acid and anisole (4:1) D-α-[[[(cyanomethyl)amino]oxoacetyl]amino]-2-thiopheneacetic acid is obtained in 74% yield. The product is recrystallized from absolute ethanol to obtain white crystals, m.p. 199–200°.

EXAMPLE 4

[(Cyanomethyl)amino]oxoacetic acid, 4-nitrophenyl ester 50 mM of [(cyanomethyl)amino]oxoacetyl chloride dissolved in methylene chloride is added dropwise at 0° to a solution of 40 mM of p-nitrophenol and 40 mM of dimethylaniline in methylene chloride. After stirring for one hour, the reaction mixture is extracted once with dilute hydrochloric acid and twice with water. The dried methylene chloride phase is concentrated under vacuum and yields 4.2 g. of [(cyanomethyl)amino]oxoacetic acid, 4-nitrophenyl ester as a brown oil which crystallizes upon trituration with ether. Recrystallization from toluene gives white crystals, m.p. 123–124°.

EXAMPLE 5

6-[[D-[[[(Cyanomethyl)amino]oxoacetyl]amino]-phenylacetyl]-amino]-3,4-dimethyl-7-oxo-4-thia-1-azabicyclo[3.2.0]-heptane-2-carboxylic acid, monohydrate 3.48 g of ampicillin, 1.01 g. of triethylamine, b 2.5 g. of [(cyanomethyl)amino]oxoacetic acid, 4-nitrophenyl ester and 1 g. of N-hydroxybenzotriazole in 50 ml. of dimethylacetamide are stirred for three hours at room temperature. 300 ml. of water are then added and the mixture is extracted with ethyl acetate. The aqueous phase, after cooling, is acidified to pH 2.5 with 2N phosphoric acid and extracted again with ethyl acetate. The organic phase is washed with water, dried and concentrated to obtain 2.7 g. of crude 6-[[D-[[[(cyanomethyl)amino]oxoacetyl]amino]phenylacetyl]-amino]-3,4-dimethyl-7-oxo-4-thia-1-azabicyclo[3.2.0]-heptane-2-carboxylic acid, monohydrate as a yellowish powder. After precipitation from tetrahydrofuran-ether, the product is obtained as a white powder, m.p. 83° (dec.)

The sodium salt is obtained as a white powder, m.p. 206° (dec.), by freeze drying an aqueous, equimolar solution of the above product and sodium bicarbonate.

EXAMPLE 6

6-[[D-[[[(Cyanomethyl)amino]oxoacetyl]amino]-2-thienylacetyl]amino]-3,3-dimethyl-7-oxo-4-thia-1-azabicyclo[3.2.0]heptane-2-carboxylic acid D-α-[[[(Cyanomethyl)amino]oxoacetyl]amino]-2-thiopheneacetic acid is dissolved in tetrahydrofuran and several drops of N-methylmorpholine are added. Then chloroformic acid isobutyl ester dissolved in tetrahydrofuran is added dropwise. After 30 minutes the reaction solution is added to a solution of 6-aminopenicillanic acid, trimethyl silyl ester and stirred. After stirring 4 hours, the solvent is removed to obtain the product, 6-[[D-[[[(cyanomethyl)-amino]oxoacetyl]amino]-2-thienylacetyl]amino]-3,3-dimethyl-7-oxo-4-thia-1-azabicyclo[3.2.0]heptane-2-carboxylic acid.

EXAMPLES 7–54

Following the procedure of Example 6 but employing the acylating agent A below having the substituents in the following table (which is prepared as described in Examples 1 to 3) and the 6-aminopenicillanic acid Compound B below, one obtains the product C having the same substituents shown in the table. Where appropriate, the protecting group and ester group are removed as in Example 4. The salts are produced as in Example 5.

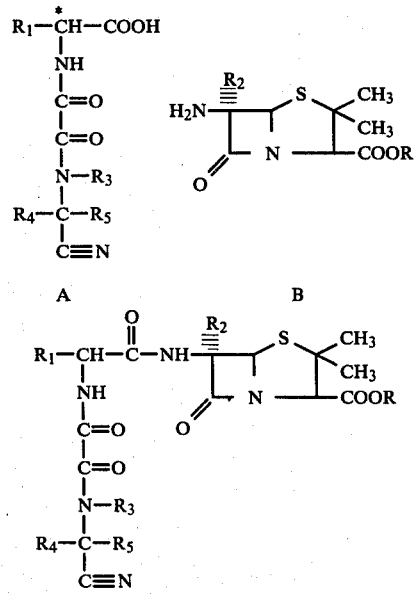

| Example | R₁ | R₂ | R | R₃ | R₄ | R₅ |
|---|---|---|---|---|---|---|
| 7 | thienyl | H | t-C₄H₉ | H | H | H |
| 8 | thienyl | H | H | H | CH₃ | H |
| 9 | thienyl | —OCH₃ | H | H | H | H |
| 10 | thienyl | —OCH₃ | H | H | H | H |
| 11 | thienyl | H | H | —CH₂—C₆H₅ | H | H |
| 12 | thienyl | H | H | —CH₂—C₆H₅ | H | H |
| 13 | phenyl | H | C₂H₅ | CH₃ | CH₃ | H |
| 14 | phenyl | OCH₃ | H | H | H | H |
| 15 | thienyl | H | —CH₂CCl₃ | C₂H₅ | H | H |
| 16 | thienyl | H | CH₃ | H | H | H |
| 17 | phenyl | H | Na | H | H | C₂H₅ |
| 18 | phenyl | —OCH₃ | K | C₂H₅ | H | H |
| 19 | pyridyl | H | H | H | CH₃ | CH₃ |
| 20 | thienyl | H | H | H | CH₃ | CH₃ |
| 21 | furyl | —OCH₃ | —C₂H₅ | —CH₃ | H | H |
| 22 | phenyl | H | H | —CH₂—C₆H₅ | H | H |
| 23 | furyl | H | H | CH₃ | H | CH₃ |

-continued
| Example | R₁ | R₂ | R | R₃ | R₄ | R₅ |
|---|---|---|---|---|---|---|
| 24 | 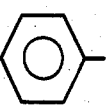 | H | H | —C₂H₅ | H | H |
| 25 | 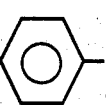 | —OCH₃ | H | H | H | CH₃ |
| 26 | 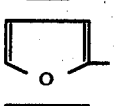 | H | K | H | H | H |
| 27 | 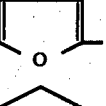 | H | Sn(CH₃)₃ | —CH₃ | H | H |
| 28 | 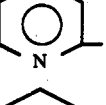 | H | t-C₄H₉ | —CH₃ | H | H |
| 29 |  | H | H | H | H | H |
| 30 | 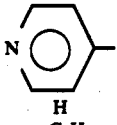 | H | K | H | H | H |
| 31 | H | H | H | H | H | H |
| 32 | —C₂H₅ | —OCH₃ | t-C₄H₉ | —C₃H₇ | H | H |
| 33 | 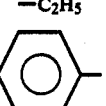 | H | —N(C₂H₅)₃ | H | H | —C₃H₇ |
| 34 | 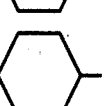 | H | H | H | H | H |
| 35 | 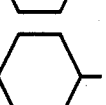 | H | K | H | H | H |
| 36 | 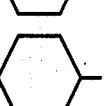 | —OCH₃ | H | H | CH₃ | H |
| 37 | 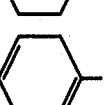 | H | H | H | H | H |
| 38 | 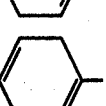 | —OCH₃ | H | H | H | H |
| 39 | 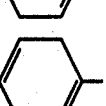 | H | t-C₄H₉ | H | H | H |
| 40 | 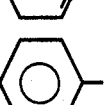 | H | H | 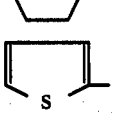 | H | H |
| 41 | 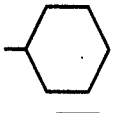 | H | H |  | H | H |

-continued

| Example | $R_1$ | $R_2$ | R | $R_3$ | $R_4$ | $R_5$ |
|---|---|---|---|---|---|---|
| 42 | cyclobutyl- | H | Na | H | H | H |
| 43 | phenyl-(CH$_2$)$_2$- | H | H | H | H | H |
| 44 | cyclopentenyl- | H | H | —CH$_3$ | H | H |
| 45 | cyclohexenyl- | —OCH$_3$ | H | H | H | H |
| 46 | cyclohexenyl- | H | —C$_2$H$_5$ | H | H | H |
| 47 | 4-HO-phenyl- | H | H | H | H | —C$_4$H$_9$ |
| 48 | 4-H$_3$C-phenyl- | H | —CH$_2$—CCl$_3$ | CH$_3$ | H | H |
| 49 | 3,4-Cl$_2$-phenyl- | H | K | H | H | H |
| 50 | 4-H$_3$CO-phenyl- | H | H | H | H | H |
| 51 | 4-HO-phenyl- | H | H | —CH$_3$— | H | —CH$_3$ |
| 52 | cyclohexadienyl- | H | Na | H | H | H |
| 53 | phenyl- | —OCH$_3$ | Si(CH$_3$)$_3$ | H | H | H |
| 54 | furyl- | —OCH$_3$ | H | H | H | H |

The acylating agents A may be in either the D- or L-form or may be a mixture of D- and L-isomers.

What is claimed is:

1. A compound of the formula

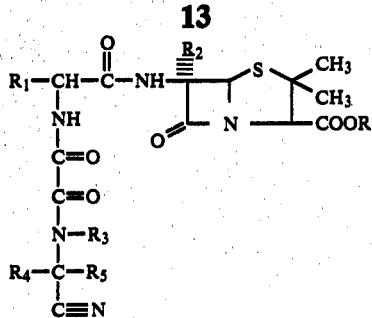

wherein R is hydrogen, lower alkyl, tri(lower alkyl)silyl, tri(lower alkyl)stannyl, trihaloethyl or a conventional penicillin salt forming ion; $R_1$ is hydrogen, lower alkyl, saturated or unsaturated cycloalkyl having up to 7 carbons and up 2 double bonds in the ring, phenyl, phenyl-lower alkyl, substituted phenyl wherein said phenyl substituent is one or two members selected from the group consisting of halogen, lower alkyl, lower alkoxy, and hydroxy, or a heterocyclic selected from the group consisting of 2-thienyl, 3-thienyl, 2-furyl, 3-furyl, 2-pyridyl, 3-pyridyl, and 4-pyridyl; $R_2$ is hydrogen or methoxy; $R_3$ is hydrogen, lower alkyl, phenyl-lower alkyl or cycloalkyl as defined above; and $R_4$ and $R_5$ each is hydrogen or lower alkyl.

2. A compound as in claim 1 wherein $R_1$ is thienyl.
3. A compound as in claim 1 wherein $R_1$ is phenyl.
4. A compound as in claim 1 wherein $R_1$ is furyl.
5. A compound as in claim 1 wherein $R_1$, $R_2$, $R_3$, $R_4$ and $R_5$ each is hydrogen.
6. A compound as in claim 1 wherein R is hydrogen or alkali metal; $R_1$ is cyclohexadienyl, phenyl, thienyl, furyl or pyridyl; $R_2$ is hydrogen or methoxy; and $R_3$, $R_4$ and $R_5$ each is hydrogen or lower alkyl.
7. A compound as in claim 1 wherein R is hydrogen, sodium or potassium; $R_1$ is phenyl or thienyl; $R_2$ is hydrogen; $R_3$ is hydrogen or methyl; and $R_4$ and $R_5$ each is hydrogen.
8. A compound as in claim 1 wherein R, $R_2$, $R_3$, $R_4$ and $R_5$ each is hydrogen; and $R_1$ is 2-thienyl.
9. A compound as in claim 1 wherein $R_1$ is phenyl; and R, $R_2$, $R_3$, $R_4$ and $R_5$ each is hydrogen.
10. A compound as in claim 1 wherein R is sodium, $R_2$, $R_3$, $R_4$ and $R_5$ each is hydrogen; and $R_1$ is phenyl.
11. The D-isomer of a compound of claim 1.
12. The D-isomer of the compound of claim 9.

* * * * *